Figure 1:
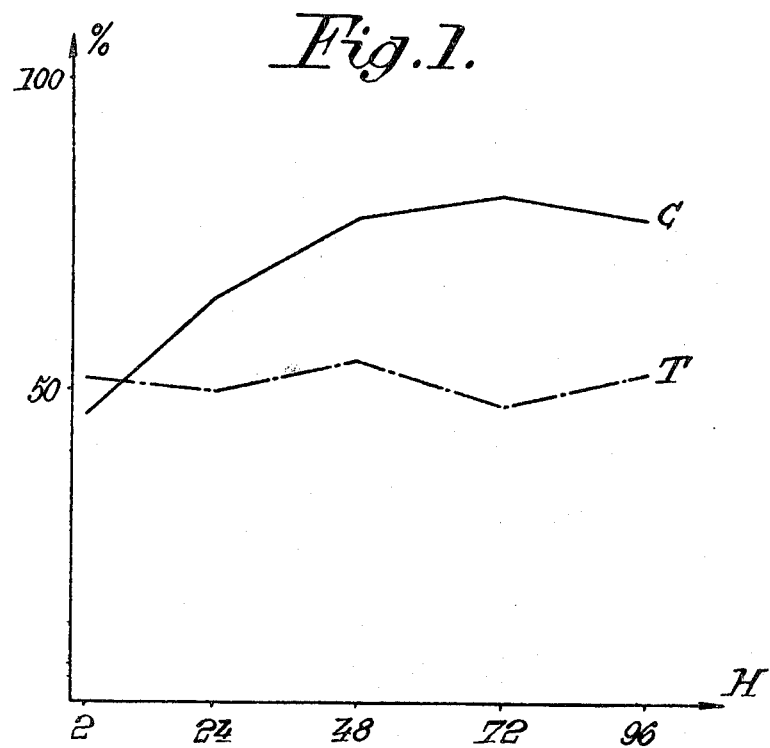

United States Patent [19]

Fauve

[11] 4,180,563

[45] Dec. 25, 1979

[54] **IMMUNOSTIMULANT AGENT FROM *SALMONELLA TYPHIMURIUM* OR *LISTERIA MONOCYTOGENES* BACTERIAL CELLS AND PHARMACEUTICAL COMPOSITION**

[75] Inventor: Robert Fauve, Sevres, France

[73] Assignee: Institut Pasteur, Paris, France

[21] Appl. No.: 880,511

[22] Filed: Feb. 23, 1978

Related U.S. Application Data

[60] Division of Ser. No. 573,925, May 2, 1975, Pat. No. 4,076,801, which is a continuation of Ser. No. 317,022, Dec. 20, 1972, abandoned.

[30] Foreign Application Priority Data

Dec. 24, 1971 [FR] France .................................. 71.46520

[51] Int. Cl.² ............................................. A61K 39/02
[52] U.S. Cl. ....................................................... 424/92
[58] Field of Search ........................................... 424/92

[56] References Cited

U.S. PATENT DOCUMENTS 3,185,624  5/1965  Nakazawa et al. .................... 424/92

*Primary Examiner*—Sam Rosen
*Attorney, Agent, or Firm*—Weiser, Stapler & Spivak

[57] ABSTRACT

An immunostimulant from bacterial cells of *Salmonella typhimurium* or *Listeria monocytogenes;* it promotes nonspecific resistance to pathogens which has no antigenic relationship to the immunostimulant.

13 Claims, 9 Drawing Figures

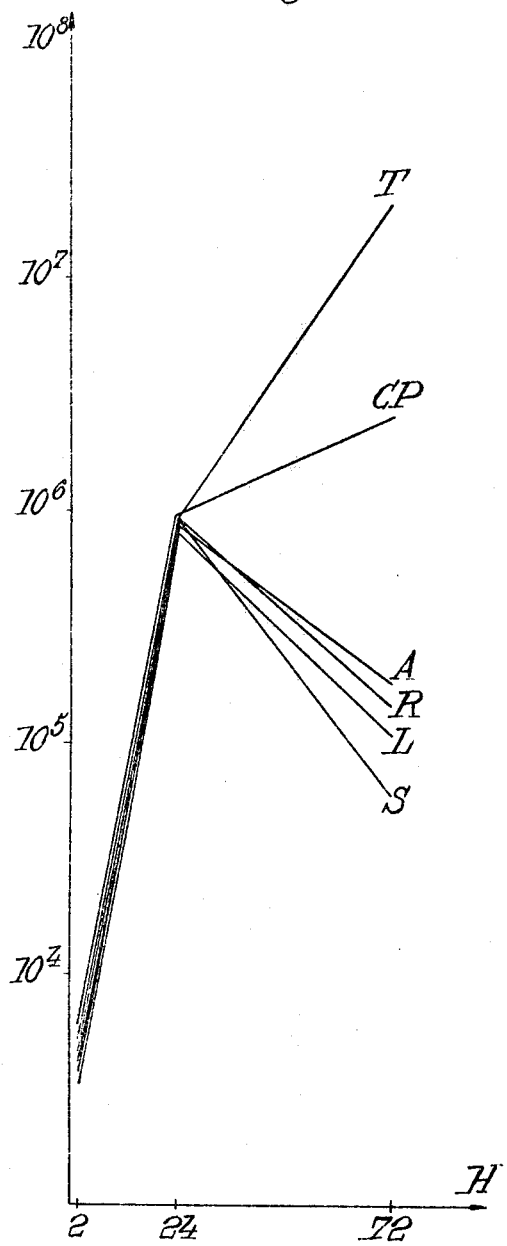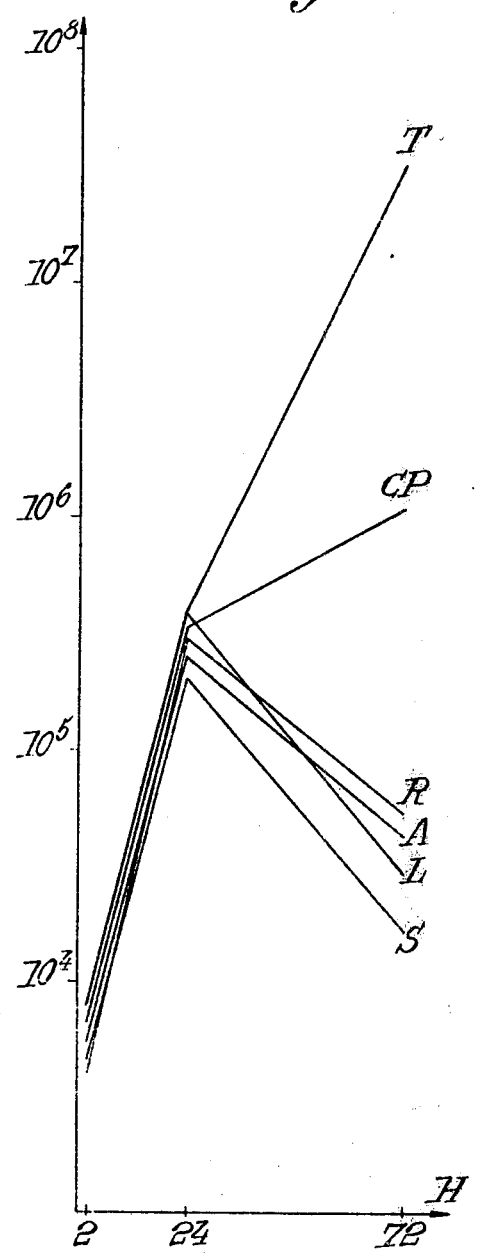

IMMUNOSTIMULANT AGENT FROM SALMONELLA TYPHIMURIUM OR LISTERIA MONOCYTOGENES BACTERIAL CELLS AND PHARMACEUTICAL COMPOSITION

This is a division of application Ser. No. 573,925, filed May 2, 1975, now U.S. Pat. No. 4,076,801, which is a continuation of U.S. Ser. No. 317,022, filed Dec. 20, 1972, now abandoned.

The invention, produced at the Pasteur Institute, relates to an agent capable of stimulating the non-specific resistance of the human or animal organism, with respect to various pathogenic agents (virus, bacteria, parasites, etc.), in the absence of antigenic relationship between the stimulant product and the infectious agent. Agents possessing this action will be denoted below, for convenience of language, by the expression "immunostimulant agents".

There are already known a certain number of substances or compositions which constitute such non-specific immunostimulant agents. Their application in human or veterinary therapeutics, has however been scarcely contemplated, by reason of their toxicity being too great and also of their action being too much delayed.

The invention rests on the discovery that a very active immunostimulant agent, with short time for taking effect and, at the same time, practically devoid of toxicity, could be easily isolated from splenic cells of animal origin, from *Ehrlich ascites* cells and from bacterial strains, or of *Bacillus subtili* cells and of *Saccharomyces cerevisiae*, this immunostimulant agent beng of such a nature as to constitute a valuable active principle for the constitution of medicaments, for example for stimulating in non-specific manner the resistance of the organism against numerous infectious agents, of the type which have been cited above.

The immunostimulant agent according to the invention is obtained from splenic cells of animal origin from *Ehrlich ascites* cells or from bacteria or of *Bacillus subtili* cells and of *Saccharomyces cerevisiae* by a method, also according to the invention, which is characterised in that there is effected a suspension of these cells or of these bacteria in a mixture of solvents containing a halogenated hydrocarbon, such as chloroform, and an alcohol, such as methanol, and that there is separated, for example by centrifugation, the insoluble fractions, that the liquid fraction is evaporated under reduced pressure and at a reduced temperature, that the solid residue is taken up again in chloroform and collected by filtration of the chloroform solution, which contains the above-mentioned immunostimulant agent.

There is advantageously used, for effecting the initial suspension of said cells in bacteria, a solution with equal parts by volume of chloroform and methanol.

Immunostimulant agents, similar in their properties, as will be seen in the rest of the description, have been obtained from cells as diverse as the splenic cells in the mouse, as is or infected by *Listeria monocytogenes*, the *Ehrlich ascites* cells or, as regards bacterial strains, *Listeria monocytogenes*, *Salmonella typhimurium*, *Escherichia coli* K 12, *Corynebacterium parvum*, etc. It will be noted that the immunostimulant agent according to the invention can be extracted from bacteria both pathogenic, (*Vibrio cholera, Mycobacterium tuberculosis, Listeria monocytogenes, Salmonella typhimurium*) and non-pathogenic (*Escherichia Coli* K 12, *Corynebacterium parvum*) or even from gram positive bacteria (*Listeria monocytogenes*) or gram negative (*Salmonella typhimurium, Escherichia Coli* K 12, and *Vibrio cholera*) and from aerobic bacteria (*Listeria monocytogenes, Salmonella typhimurium, Escherichia coli* K 12, *Mycobacterium tuberculosis*) or anaerobic bacteria (*Corynebacterium parvum*). It can also be obtained from *Bacillus subtilis* and *Saccharomyces cerevisiae*.

It is to be noted that the immunostimulant agent according to the invention has not been obtainable from cells of animal origin other than splenic cells. An explanation which can only be of hypothetical value, it is the bacteria entering accidentally into the blood circulation and which are blocked at the level of the splenic microphages which account for the activity of the extracts of splenic origin. These same bacteria should then normally be stored also at the level of the hepatic macrophages. It has however already been established and shown that certain microbial antigenes are destroyed by the hepatic macrophages, whilst they remain intact at the level of the splenic macrophages.

The invention relates also to a suspension of the immunostimulant agent contained in a liquid vehicle of the type which are used for constituting injectable suspensions, the immunostimulant agent according to the invention occurring here in the form of particles of sufficiently small dimensions, for example less that 20 microns, so that the suspension obtained can be in fact injectable, in the absence of any counter-indication.

It relates also to a method for forming this injectable solution, which method is characterised in that the immunostimulant agent according to the invention is placed, in the form of its solution in one of its solvents, for example, chloroform, in contact with the abovesaid injectable vehicle, for example an 8.5°/$_{oo}$ solution of sodium chloride, that there is made to bubble through the mixture a gas inert with respect to the constituents of the chloroform solution until the complete elimination of the chloroform, and that there then follows a homogenisation of the suspension obtained to reduce the solid particles retained in the aqueous solution, to dimensions which permit the injection of the suspensions into the animal or man.

By lyophilisation of this suspension there is obtained a hygroscopic, yellowish compact residue, which softens and becomes a pasty mass in air. This residue can be taken up again in chloroform.

Advantageously the volumes of the chloroform solution and of the injectable aqueous solution placed in contact are adjusted so that the aqueous suspension finally obtained contains between about 105 and 275 mcg by dry weight/ml.

Other characteristics of the invention will appear also in the course of the description of a preferred embodiment of the method according to the invention to obtain the desired immunostimulant agents from a certain number of sources indicated by way of example, and from pharmacological experiments which have enabled the establishment of the particularly interesting properties of these immunostimulant agents. The various results of these pharmacological experiments are also expressed in graphical form in the drawings.

In order to obtain first of all an immunostimulant agent from specimens of:
  splenic cells of the mouse
    splenic cells of the mouse infected with *Listeria monocytogenes* (Serotype I, No. 54,149 of the Collection of the Pasteur Institute)

*Listeria monocytogenes* (coming from the above-mentioned numbered strain)

*Salmonella typhimurium* (strain C5 of the Collection of the Pasteur Institute)

*Escherichia coli* K 12 (strain No. C.600 of the Collection of the Pasteur Institute)

*Corynebacterium parvum* (strain No. 936 B of the Collection of the Pasteur Institute)

*Mycobacterium tuberculosis* (strain BCG of the Pasteur Institute)

*Vibrio cholera* (strain of the Pasteur Institute)

*Bacillus subtilis*

*Saccharomyces cerevisiae* the procedure is as follows or in analogous manner:

To a volume of a specimen to be treated there are added ten volumes of a mixture of equal volumes of chloroform and of methanol. The mixture obtained is homogenised by means of a grinder for two hours at +4° C. and is then centrifuged at 3,500 G for twenty minutes. The supernatant liquid is taken up in a flask and evaporated under vacuum (water pump) at a temperature of 40° C. The flask is then filled with a volume of chloroform double that of the initial specimen and subjected to a rotary speed of 40 revolutions per minute for thirty minutes. After this time, the chloroform solution is filtered on a Whatman No. 3 paper. The filtrate, which contains the desired immunostimulant agent, can be preserved at +4° C. in a glass bottle.

The substances which form the immunostimulant agent according to the invention, and which are soluble in chloroform, are not however soluble in water. An injectable suspension of this agent can however be obtained, by starting from the above-mentioned chloroform solution, for example by proceeding as follows:

There is introduced into a tube a predetermined volume of the above-mentioned chloroform solution, there is added thereto a volume, also predetermined, of an apyrogenic solution of $8.5°/_{oo}$ of sodium chloride. There is then made to bubble therethrough a gas inert with respect to the constituents of the liquid mixture, this gas being constituted for example by nitrogen or by a mixture of 95% air and 5% of carbon dioxide, by means of a glass tube dipping, inside the tube, just into the chloroform phase, this bubbling being pursued until the complete elimination of chloroform. The immunostimulant agent initially contained in the chloroform solution passes, in the course of this bubbling operation, into suspension in the aqueous phase. This suspension is then homogenised to reduce the dimensions of the particles in suspension. In the laboratory, this homogenisation can be carried out by means of a syringe provided with a needle of diameter less than 0.4 mm, by successive aspirations and expulsions, until the suspension no longer contains corpuscles of a diameter greater than 20 microns. This suspension is opalescent. It is this which has been used in the pharmacological tests whose description follows.

These tests have been carried out in mice which come, either from the N.C.S. Colony of the Service of Experimental Pathology of the Pasteur Institute, or from the Breeding Centre of the CNRS of Orleans la Source. The animals used were of both sexes, their age comprised between three and five weeks, their weight comprised between fifteen and twenty grams.

The effects which are described below have all been obtained by the injection into these mice, of 0.5 ml of a suspension of the type described above, by the intravenous, subcutaneous or intraperitoneal route. These injections have never been followed by visible toxic effect, either immediately, or five months later.

A—Protection of mice against infection by *Listeria monocytogenes* and *Salmonella typhimurium*

The infections were performed by means of the strain of *Listeria monocytogenes*, scrotype I, No. 54,149 in the Collection of the Pasteur Institute, and by the strain *Salmonella typhimurium* (strain C5 of the Collection of the Pasteur Institute), in groups of mice which had received by injection, some by the intravenous route, others by the intraperitoneal route, doses of 0.5 ml of the suspensions of the immunostimulant agents respectively prepared from various animal or bacterial sources mentioned above, as well as into control groups of mice.

The mice previously treated with the immunostimulant agent by the intraperitoneal route withstand a dose of *Listeria monocytogenes* equal to ten times the lethal 50 dose ($LD_{50}$) of the same pathogenic agent in the controls; those treated by the intravenous route at the very high dose of 75 times the $LD_{50}$ of the pathogenic agent.

In the same way, the mice which have previously received the immunostimulant agent by the intravenous route, resist a dose of the order of twenty times greater than the $LD_{50}$ observed in the controls, of the pathogenic agent *Salmonella typhimurium*. This protection is still greater if the mice are treated by the oral route. They then resist a dose of the pathogenic agent equal to 100 times the $LD_{50}$ observed in the controls.

The protection of the mice is ensured in efficacious manner, even when they are only treated with the immunostimulant agent three hours before the infection. The protection then still persists 30 days later.

B—Influence of intraperitoneal injection of the immunostimulant agent extracted from *Listeria monocytogenes* on the weight of the spleen and of the thymus as well as on the peritoneal cells These experiments were carried out in N.C.S. mice of five weeks.

1—Weight of spleen: injection of product is not followed by variation in the weight of the spleen between two hours and four days after treatment.

2—Weight of the thymus: here again, no variation in weight was observed.

3—Quantitative and qualitative variations in the peritoneal cells: examination of these cells was carried out after exsanguination of the mice and injection into the peritoneal cavity of 5 ml of a mixture containing 2% of bovine albumin and five units of heparin per ml according to the technique described in Science 1968, 160, 795.

The following results were observed as regards the variation in the number of macrophages, of polynuclear cells and of lymphocytes as a function of time:

a—Macrophages: After a drop of about 50%, the number of macrophages increases from the twenty-fourth hour and is maintained at a higher level than in the control animals.

The spreading of the macrophages (percentage of macrophages spread out) increases until the forty-eighth hour after the injection of the immunostimulant agent, and remains high up to the fourth day.

b—Polynuclear cells: Their presence in the peritoneal cavity has only been noted at the twenty-fourth hour and their number was but slightly increased.

c—Lymphocytes: After a slight reduction, their number increases substantially, three days after the injection.

It is to be noted that in the course of this examination, there has not been observed a reduction in the percentage of spreading out of the macrophages and that, even four days after the injection, the peritoneal macrophages do not show a notable increase in the number of their lysozomes. In the same way, the increase in the number of cells is relatively discrete (an increase less than 100%). These facts distinguish these results from that which is known with conventional immunostimulants which are B.C.G. and the endotoxines.

Figure 1A:
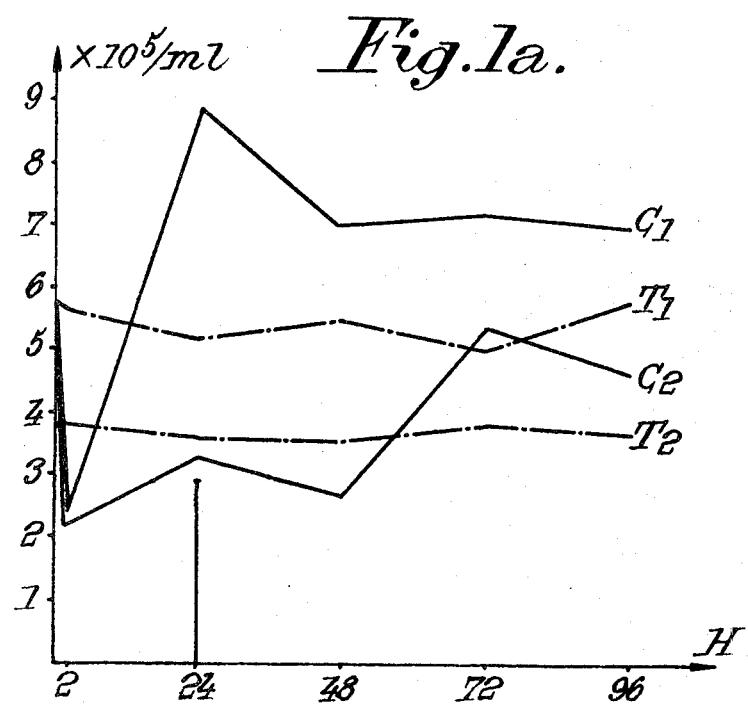

These results are expressed graphically in FIGS. 1 and 1a in which there appear:

in FIG. 1: the variation in the percentage of flattened macrophages as a function of the time which has elapsed after the injection of the immunostimulant agent into the treated animals (curve C) and of the physiological serum in the controls (curve T);

in FIG. 1a: the variations as a function of the time, after the injection, of the number of macrophages per ml in the treated animals (curve $C_1$) and the controls (curve $T_1$), on the one hand, of the number of lymphocytes in the treated animals (curve $C_2$) and the controls (curve $T_2$), on the other hand.

C—Influence of an intravenous injection of the immunostimulant agent extracted from *Listeria monocytogenes* on the weight of the spleen and of the thymus, on the blood cells and on the peritoneal cells 1—Weight of the spleen and of the thymus As previously, there was not any change in weight of these organs.

2—Blood count and composition

The injection of the product was not followed by leucopenia and no really important leucocytosis was observed.

3—Quantitative and qualitative variations of the peritoneal cells a—Macrophages

From the twenty-fourth hour after injection, and up to the fourth day, the number of macrophages is slightly greater in the treated mice than that of the macrophages in the control mice.

The percentage of flattening of the macrophages is from the very first higher than that of the control macrophages, and it remains so until the end of the observation period.

b—Lymphocytes

After a slight reduction in their number, there is noted an increase, which is especially marked forty-eight hours after the injection and returns to a normal value twenty-four hours later.

Figure 2:
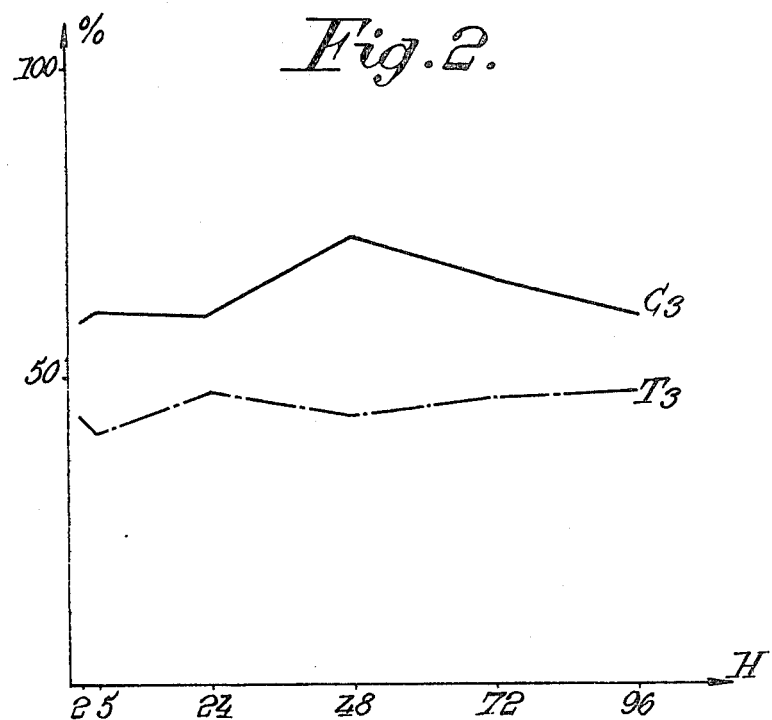
Figure 2A:
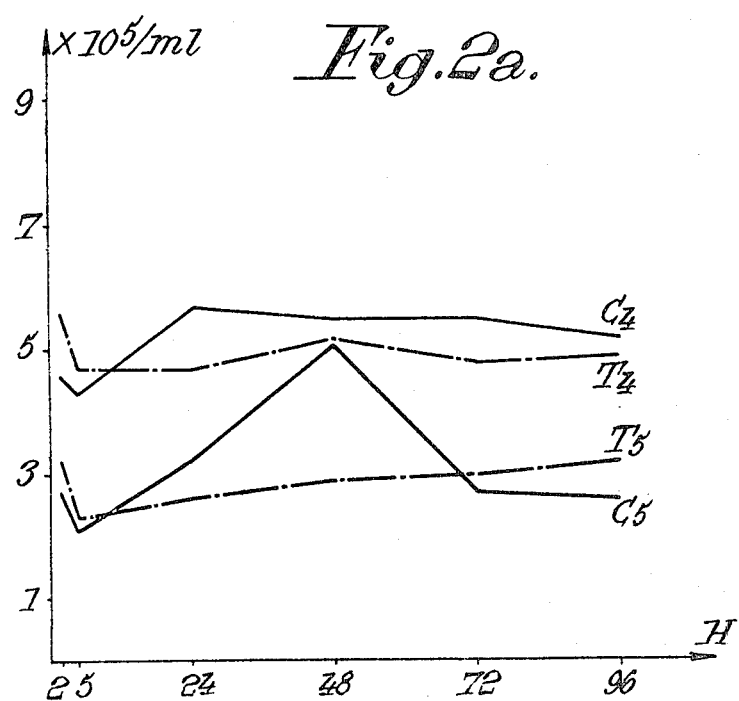

These results are expressed graphically in FIGS. 2 and 2a, in a similar manner to that which has already been indicated with respect to FIGS. 1 and 1a. They show:

the variation in the percentage of flattened macrophages as a function of the time in the treated animals (curve $C_3$) and the controls (curve $T_3$);

the variation as a function of time of the number of macrophages in the treated animals (curve $C_4$) and the controls ($T_4$) on one hand, and the number of lymphocytes in the treated animals (curve $C_5$) and the controls (curve $T_5$) on the other hand.

D—Removal from blood of *Salmonella typhimurium*

In the course of experiments carried out, the mice which were treated previously with the immunostimulant agent according to the invention, underwent and injection by the intravenous route of a suspension of *Salmonella typhimurium* $C_5$ containing $1 \cdot 3 \cdot 10^7$ to $1 \cdot 9 \cdot 10^7$ living bacteria. Two minutes and two hours after the infection, the mice were anesthesed with ether, the blood was removed through the axillary artery and, after suitable dilution, the specimens were sown on nutritive gelose. It was thus possible to know, two minutes and two hours after the infection, the quantity of bacteria present in the blood of the animals.

Figure 3:
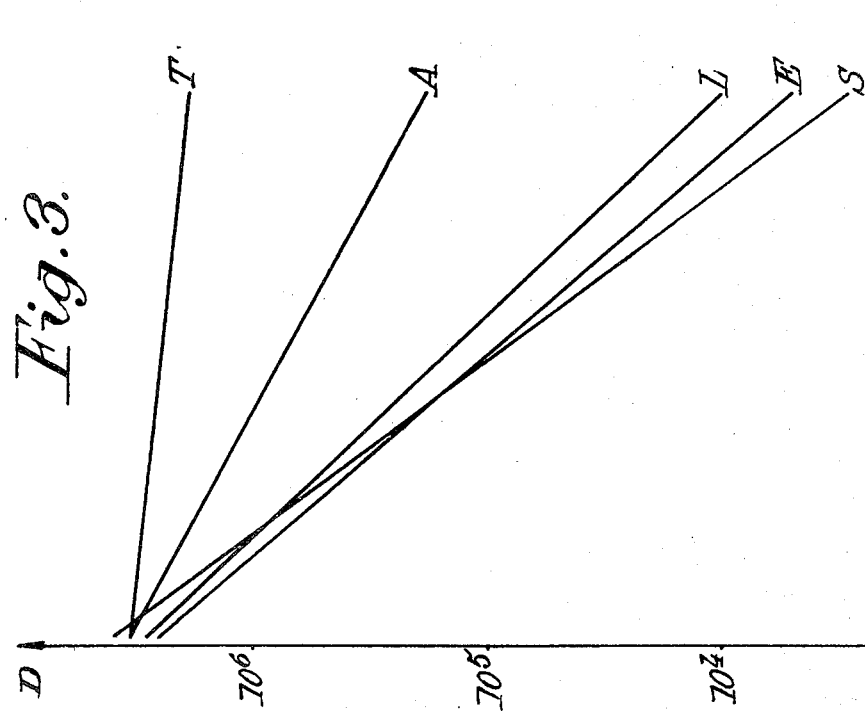

There is reproduced graphically in FIG. 3, the results obtained under the effect of immunostimulant agents extracted from the aforesaid starting materials, more particularly the slopes representing the decrease D in the blood content of the above-mentioned living bacteria, as a function of time, in the presence of immunostimulant agents extracted from *Ehrlich ascites* cells (curve A), from *Listeria monocytogenes* (curve L), from *Salmonella typhimurium* (curve S), from *Escherichia coli* K 12 (curve E) as well as for the controls (curve T).

The acceleration in the removal from the blood of Salmonellae is already marked with the extract of *Ehrlich ascites* cells (1 log 10 of separation with respect to the controls) but this acceleration is really considerable with the extracts of *Listeria monocytogenes*, of *Escherichia coli* K 12, and *Salmonella typhimurium* (3 log 10 with respect to the controls). A similar acceleration was obtained with extracts of *Vibrio cholera* and BCG. We note here that the difference is only 4 log 10 in mice which were immunised specifically against *Salmonella typhimurium*.

Figure 4:
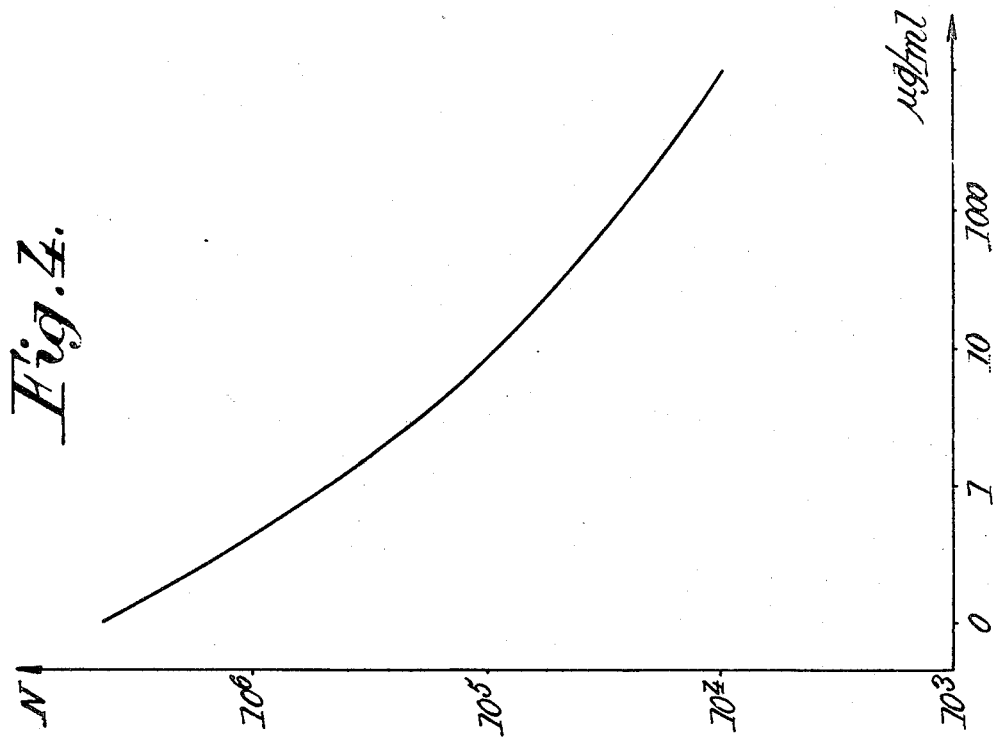

It was investigated whether there existed a relationship between the amount of immunostimulant agent injected and the intensity of this elimination from the blood of bacteria. To this end, there was injected into four groups of five mice, by the intravenous route, 0.5 ml of the suspension containing respectively 1, 10, 100 and 1,000 μg of immunostimulant agent. In parallel, a group of control mice received injections of physiological serum by the same route. Fifteen hours later, there was injected, by the intravenous route, $5 \times 10^7$ *Salmonella typhimurium* in each of the mice. Two hours after the infection, the blood of these animals was removed and bacterial counts were carried out. FIG. 4 establishes graphically, the reduction in the effects of the immunostimulant agent, expressed by the number N of bacteria found in the blood at the time of the bacterial count, as a function of its concentration. The regular decrease observed denotes the existance of a correlation between the dose of immunostimulant agent injected and the acceleration of the elimination from the blood of bacteria.

It was also noted that the incorporation of an immunostimulant agent, extracted from *Salmonella typhimurium*, in a calcium phosphate gel, can, when it is injected by the subcutaneous route fifteen hours before the infection, involve an acceleration in the elimination of the bacteria, which demonstrates its very great activity. It was also noted that the immunostimulant agent does not lose its activity when it is heated fifteen minutes at 100° C.

E—Fate of *Listeria monocytogenes* in the liver and the spleen of the mouse

It has already been established that a prior injection of the immunostimulant agent, extracted from *Listeria monocytogenes* or from *Ehrlich ascites* cells, involves a certain protection against infection with *Listeria monocytogenes*. It is possible to quantify in more specific manner the response of the mouse to this infection by carrying out bacterial counts in the spleen and the liver of these animals, given that the Listeria only develops in the macrophages of these organs.

These tests were carried out on six groups of mice which had previously, received respectively subcutaneous injections of 0.5 ml of the suspension of the following immunostimulant agents:

*Listeria monocytogenes* (L), *Corynebarterium parvum* (CP), *Salmonella typhimurium* (S), *Ehrlich ascites* cells (A), spleen of the mouse (R), sixth group (T) only received 0.5 ml of 8.5 g°/$_{oo}$ sodium chloride.

All these mice were injected eighteen hours later by the intravenous route with *Listeria monocytogenes* bacteria, in the dose of 8·10$^4$ of *Listeria monocytogenes* bacteria. The animals are then sacrificed by cervical section, respectively 2, 24 and 72 hours after the infection; the livers and spleens were removed, ground and, after dilution, sown on gelose. It is then possible to know at a given moment, the number of living Listeria present in the liver and the spleen.

FIGS. 5 and 5a give a graphical representation of the observed phenomena. There is shown there the variation, as a function of time, expressed in hours, of the number of *Listeria monocytogenes* bacteria found in the spleen and the liver respectively of these animals.

The graphs show the number of bacteria found two hours after infection substantially of the same order of magnitude in the six groups of mice. In the same way, twenty-four hours after infection, the results obtained do not permit a conclusion of beneficial action of the extracts. On the contrary, seventy-two hours later there were noted very marked differences. In fact, although spleens and livers of the control mice contain more than 10$^7$ bacteria, there was found in the spleen of the animals treated with immunostimulant agents extracted from Listeria, from *Salmonella typhimurium*, from *Ehrlich ascites* cells, and from the spleens of mice, 100 times less bacteria and, in the liver of the same animals, 1,000 times less germs. The effect of the immunostimulant agent extracted from *Corynebacterium parvum*, weaker, remains none-the-less distinct.

Comparable results were observed when the immunostimulant agent originated from *Vibrio cholera* or from *Mycobacterium tuberculosis* strain BCG. Moreover, there exists there also a correlation between the dose of the immunostimulant agent injected and the effect noted.

F—Effects on the sensitivity to bacterial endotoxines

The immunostimulant agents according to the invention do not increase the sensitivity of mice to bacterial endotoxines, as the following tests have shown:

Three groups of five mice received, by intravenous injection, 0.5 ml of a suspension of the immunostimulant agent extracted from *Listeria monocytogenes*. In the same way, three control groups received, by intravenous injection, 0.5 ml of a 8.5°/$_{oo}$ solution of sodium chloride. The groups of each category were inoculated twenty-four hours later with, respectively, 10, 100 and 500 micrograms of bacterial endotoxines. It was noted that the mice of the test groups survived under the same conditions as those of the control groups.

G—Increase in the resistance of the mice treated by the immunostimulant agent towards Streptolysine O Three groups of five mice received, by intravenous injection, 0.5 ml of a suspension containing 100 μg of immunostimulant agent extracted from *Salmonella typhimurium* C5. Similarly, three control groups received, by intravenous injection, 0.5 ml of an 8.5°/$_{oo}$ solution of sodium chloride. The groups of each category were inoculated twenty-four hours later with doses of Streptolysine O respectively equal to 2, 3 and 4 times their LD$_{50}$. Although all the control mice died within a maximum period of an hour, the mice tested with 2 LD$_{50}$ of Streptolysine O survived, the mice tested with 3 LD$_{50}$ survived six hours and the mice tested with 4 LD$_{50}$ died at the same time as the control mice.

These tests, added to those which have been already indicated, especially as regards the effect of the immunostimulant agents according to the invention on the peritoneal and blood cells of the mouse, confirm their lack of toxicity.

The considerable acceleration, under the effect of immunostimulant agents according to the invention, of the speed of elimination of a bacterial inoculum injected by the intravenous route and this, even when the animals are infected fifteen hours later, in the same way as the capacity of the treated mice to resist infections caused by *Listeria monocytogenes*, show the importance of their anti-infectious effect. It is known in particular that animals which are protected against infection by *Listeria monocytogenes* are also capable of resisting various infections caused by the injection of bacteria or of parasites capable of multiplying inside the macrophages (brucellae, salmonellae, mycobacteria, toxoplasms . . . ). It was also noted that immunostimulant agents extracted from *Salmonella typhimurium* protects mice against 1,000 mortal doses of bacillae pesteux, when the latter are administered by the subcutaneous route.

H—Action of the immunostimulant agent on blastic transformation in vitro of lymphocytes of the spleen of the mouse Mice spleens previously removed are dissociated in Hanks liquid and the cellular suspension thus obtained is filtered on a sieve whose mesh has a cross-section of 60 microns. There was then introduced into microtubes for tissue cultures, 0.5 ml of a cellular suspension in the medium 199 containing between $0.5 \times 10^6$ and $10^7$ cells, 0.05 ml of human serum and 0.05 ml of a suspension in water of the immunostimulant agent. Various tests were carried out with increasing concentrations of the immunostimulant agent and comprised between 10 and 500 μg/ml.

Forty-two hours later, there was added 0.05 ml of a solution containing thymidine tritiated in the proportion of 10 microcuries/ml. Four hours later the tubes were centrifuged at 1,500 g for ten minutes. The centrifugation residue was restored into suspension in 0.5 ml of physiological serum.

0.5 ml of 10% chloracetic acid was added; the precipitate was collected on a Whatman GS/C filter under a suction of 60 cm of water. After rinsing the filter and the tube with 5% trichloracetic acid and 1 ml of 90° ethyl alcohol, and drying of the precipitate on its filter, the latter were introduced into a counting bottle. The counter proper is carried out in a liquid scintillation counter. This counting provides the milotic index, which is constituted by the ratio of the number of disintegrations observed in the cultures in the presence of the immunostimulant agent to the number of disintegrations observed in the control cultures.

Figure 6:
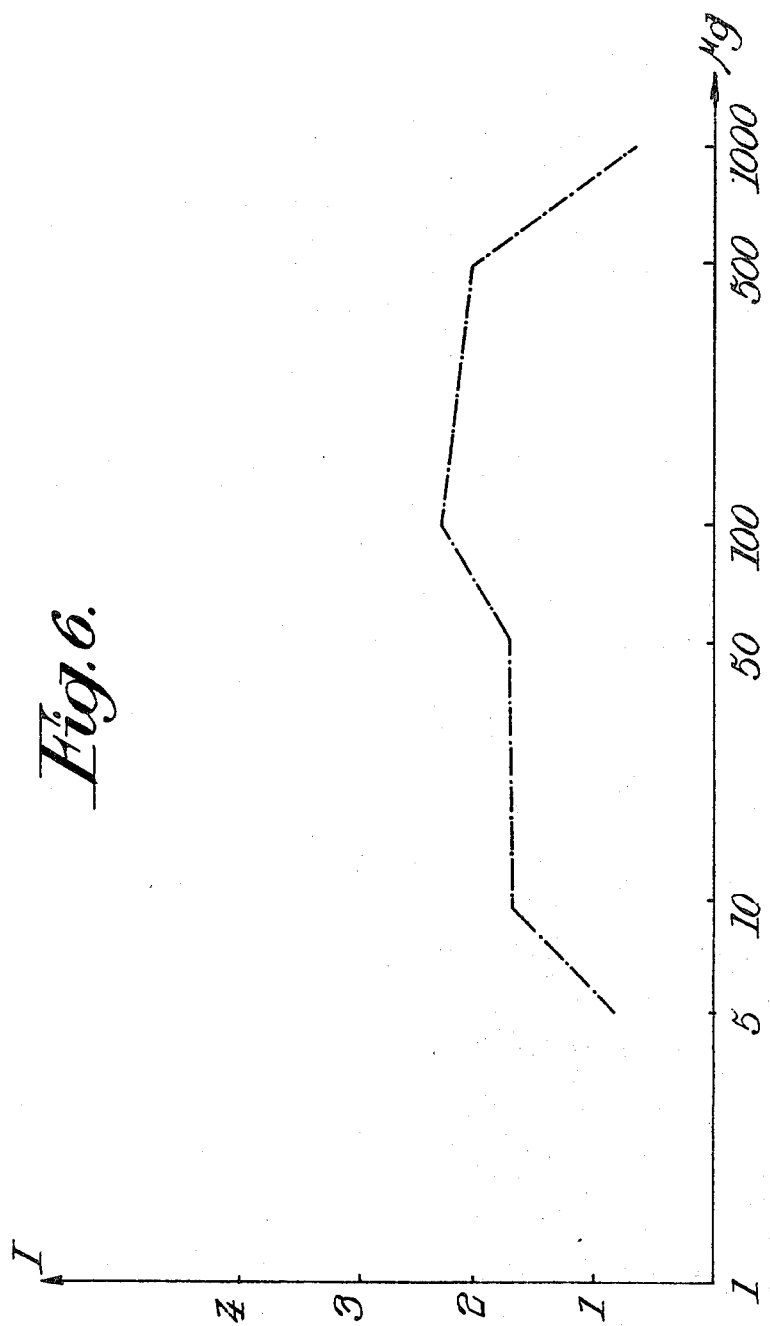

The curve of FIG. 6 gives the variations in the milotic index (I) as a function of the concentration of the immunostimulant agent (in µg/ml). FIG. 6 shows a distinct activity of the immunostimulant agent at concentrations comprised between 10 and 500 µg/ml.

It is to be noted that the immunostimulant agents extracted from *Bacillus subtilis* and from *Saccharomyces cerevisiae* have shown a similar behaviour to that observed in the preceding pharmacological tests.

The immunostimulant agents according to the invention can constitute the active principle of medicaments indicated, especially for the treatment or prevention in man or in the animal of infectious deseases caused by bacterial and even viral germs, for example infections of the type of tuberculosis, pasteurelloses, brucellosen, listerioses or infections due to gram negative bacteria. They could also be used for the treatment of toxic infections. By reason of their rapidity of action, the immunostimulant agents can be used for the prevention of post-surgical bacterial infections of any type.

They can be administered by the intravenous, intramuscular or subcutaneous route, in suspension in pharmaceutically acceptable and sterile liquid vehicles, such as solutions of physiological serum (saline solution or glucose serum), at unit doses which, when these immunostimulant agents are applied in man, can be comprised between about 0.5 and about 50 mg, for example between 1 and 10 mg.

They could also be incorporated in a gel adapted to be administered by the intradermal, subcutaneous or intramuscular route, for example a calcium phosphate gel.

In the following there is given an example of the preparation of a gel containing the immunostimulant agent and adapted to be administered by the above-indicated routes.

To 40 ml of a suspension of physiological serum containing the immunostimulant agent in suspension at the desired concentration, there is added 5 ml of a solution of anhydrous sodium phosphate $Na_2HPO_4$, containing 7.92 g of sodium phosphate per 100 ml, and 5 ml of a calcium chloride solution, containing 8 g of anhydrous calcium chloride per 100 ml.

The precipitate obtained is centrifuged and is taken up in apyrogenic physiological serum so as to obtain the desired concentration of the immunostimulant agent.

It can also be administered by the oral route, when it is associated with pharmaceutically acceptable solid or liquid excipients. Its administration can also be envisaged by the rectal route, when it is associated with excipients suitable for this mode of administration. Its external administration can also be envisaged, for example in the form of an aerosol with a vehicle suitable for this type of administration, for example for the treatment of nasal infections.

I claim:
1. An immunostimulant agent from bacterial cells of *Salmonella typhimurium* or *Listeria monocytogenes*, which immunostimulant promotes non-specific resistance to pathogens, and is
    (a) soluble in chloroform;
    (b) insoluble in water;
    (c) free of the bacterial cell fractions which are not soluble in a solvent mixture of a halogenated hydrocarbon and an alcohol;
    (d) a stimulant for the non-specific resistance of a human or animal host organism to a pathogen which has no antigenic relationship to the immunostimulant;
    (e) capable of causing an increase of macrophages and lymphocytes of a host organism;
    (f) effective against *Salmonella typhirium* in blood of so injected mice;
    (g) effective against *Listeria monocytogenes* in liver and spleen of so injected mice;
    (h) is effective against 10 times the $LD_{50}$ of *Listeria monocytogenes* and 20 times the $LD_{50}$ of *Salmonella typhimurium;*
    (i) virtually free of toxicity; and
    (j) is not capable of increasing the sensitivity of mice to bacterial endotoxins.
2. The immunostimulant of claim 1 wherein the immunostimulant is from *Salmonella typhimurium*.
3. The immunostimulant of claim 1 wherein the immunostimulant is from *Listeria monocytogenes*.
4. The immunostimulant of claims 2 or 3, wherein the immunostimulant is free of toxicity in mice in a dosage of 0.5 ml of an aqueous suspension containing between about 105 and 275 mcg by dry weight per ml of said agent.
5. A solution of the immunostimulant of claim 1 in chloroform.
6. A suspension of the immunostimulant of claim 1 in an aqueous solution.
7. The lyophilisate of the suspension of claim 6.
8. A pharmaceutical composition which comprises an acceptable carrier and in an effective amount, the immunostimulant of claim 1.
9. The pharmaceutical composition of claim 8 which is an injectable suspension of particles of the immunostimulant wherein the immunostimulant is in particles of a size adequately small to be injectable in man or animal.
10. The pharmaceutical composition of claim 9 wherein the carrier is an apyrogenic sodium chloride solution.
11. The pharmaceutical composition of claim 9 wherein the particles are of a diameter not greater than 20 microns.
12. The pharmaceutical composition of claim 10 or 11 wherein the immunostimulant is from *Salmonella typhimurium*.
13. The pharmaceutical composition of claims 10 or 11 wherein the immunostimulant is from *Listeria monocytogenes*.

* * * * *